(12) United States Patent  (10) Patent No.: US 7,471,202 B2
Anderson  (45) Date of Patent: Dec. 30, 2008

(54) CONFORMAL COIL ARRAY FOR A MEDICAL TRACKING SYSTEM

(75) Inventor: Peter Traneus Anderson, Andover, MA (US)

(73) Assignee: General Electric Co., Schenectady, NY (US)

( * ) Notice: Subject to any disclaimer, the term of this patent is extended or adjusted under 35 U.S.C. 154(b) by 289 days.

(21) Appl. No.: 11/277,821

(22) Filed: Mar. 29, 2006

(65) Prior Publication Data

US 2007/0238980 A1  Oct. 11, 2007

(51) Int. Cl.
*G08B 13/14* (2006.01)
(52) U.S. Cl. .............. 340/572.1; 340/572.7; 340/572.8; 600/424
(58) Field of Classification Search .............. 340/572.1, 340/572.7, 572.8, 825.49, 505, 10.1, 573.1; 600/424; 343/878, 895
See application file for complete search history.

(56) References Cited

U.S. PATENT DOCUMENTS

| 3,121,228 A | 2/1964 | Kalmus |
| 3,392,390 A | 7/1968 | Schelisch |
| 3,529,682 A | 9/1970 | Coyne et al. |
| 3,828,867 A | 8/1974 | Elwood |
| 3,868,565 A | 2/1975 | Kuipers |
| 3,983,474 A | 9/1976 | Kuipers |
| 4,054,881 A | 10/1977 | Raab |
| 4,176,662 A | 12/1979 | Frazer |
| 4,314,251 A | 2/1982 | Raab |
| 4,613,866 A | 9/1986 | Blood |
| 4,618,822 A | 10/1986 | Hansen |
| 4,622,644 A | 11/1986 | Hansen |
| 4,642,786 A | 2/1987 | Hansen |
| 4,710,708 A | 12/1987 | Rorden et al. |
| 4,737,794 A | 4/1988 | Jones |
| 4,742,356 A | 5/1988 | Kuipers |
| 4,812,812 A | 3/1989 | Flowerdew et al. |
| 4,820,041 A | 4/1989 | Davidson et al. |
| 4,849,692 A | 7/1989 | Blood |
| 4,945,305 A | 7/1990 | Blood |
| 5,099,845 A | 3/1992 | Besz et al. |
| 5,107,746 A | 4/1992 | Bauer |
| 5,172,056 A | 12/1992 | Voisin |
| 5,211,165 A | 5/1993 | Dumoulin et al. |

(Continued)

FOREIGN PATENT DOCUMENTS

| EP | 0531081 A1 | 3/1993 |
| WO | WO9811504 | 3/1998 |
| WO | WO02098273 A2 | 12/2002 |

OTHER PUBLICATIONS

Peter T. Anderson, "A Source of Accurately Calculable Quasi-Static Magnetic Fields," Ph.D. thesis, University of Vermont, Burlington, VT 05405, Oct. 2001.

(Continued)

*Primary Examiner*—Thomas J Mullen

(57) ABSTRACT

Described herein are one or more implementations for reducing the effects of distortion caused by the distorters in medical image-capture components used in medical electromagnetic tracking system. Examples of a medical image-capture component include an X-ray image detector used in fluoroscopic image-guided medical procedures and a surgical microscope. With one or more implementations described herein, the electromagnetic receiver unit (or transmitter unit) is conformably attached to the medical image-capture component.

15 Claims, 3 Drawing Sheets

U.S. PATENT DOCUMENTS

| | | |
|---|---|---|
| 5,245,307 A | 9/1993 | Klaus et al. |
| 5,251,635 A | 10/1993 | Dumoulin et al. |
| 5,255,680 A | 10/1993 | Darrow et al. |
| 5,265,610 A | 11/1993 | Darrow et al. |
| 5,289,373 A | 2/1994 | Zarge et al. |
| 5,307,072 A | 4/1994 | Jones, Jr. |
| 5,307,808 A | 5/1994 | Dumoulin et al. |
| 5,377,678 A | 1/1995 | Dumoulin et al. |
| 5,425,367 A | 6/1995 | Shapiro et al. |
| 5,425,382 A | 6/1995 | Golden et al. |
| 5,437,277 A | 8/1995 | Dumoulin et al. |
| 5,443,066 A | 8/1995 | Dumoulin et al. |
| 5,445,150 A | 8/1995 | Dumoulin et al. |
| 5,453,686 A | 9/1995 | Anderson |
| 5,457,641 A | 10/1995 | Zimmer et al. |
| 5,517,195 A | 5/1996 | Narlow et al. |
| 5,558,091 A | 9/1996 | Acker et al. |
| 5,592,939 A | 1/1997 | Martinelli |
| 5,600,330 A | 2/1997 | Blood |
| 5,622,169 A | 4/1997 | Golden et al. |
| 5,640,170 A | 6/1997 | Anderson |
| 5,646,524 A | 7/1997 | Gilboa |
| 5,676,673 A | 10/1997 | Ferre et al. |
| 5,715,042 A | 2/1998 | Milani et al. |
| 5,767,669 A | 6/1998 | Hansen et al. |
| 5,782,765 A | 7/1998 | Jonkman |
| 5,800,352 A | 9/1998 | Ferre et al. |
| 5,803,089 A | 9/1998 | Ferre et al. |
| 5,829,444 A | 11/1998 | Ferre et al. |
| 5,847,976 A | 12/1998 | Lescourret |
| 5,873,822 A | 2/1999 | Ferre et al. |
| 5,913,820 A | 6/1999 | Bladen et al. |
| 5,953,683 A | 9/1999 | Hansen et al. |
| 5,967,980 A | 10/1999 | Ferre et al. |
| 6,052,610 A | 4/2000 | Koch |
| 6,073,043 A | 6/2000 | Schneider |
| 6,129,667 A | 10/2000 | Dumoulin et al. |
| 6,129,668 A | 10/2000 | Haynor et al. |
| 6,161,032 A | 12/2000 | Acker |
| 6,172,499 B1 | 1/2001 | Ashe |
| 6,175,756 B1 | 1/2001 | Ferre et al. |
| 6,177,792 B1 | 1/2001 | Govari et al. |
| 6,188,355 B1 | 2/2001 | Gilboa |
| 6,201,387 B1 | 3/2001 | Govari |
| 6,201,987 B1 | 3/2001 | Dumoulin |
| 6,203,493 B1 | 3/2001 | Ben-Haim |
| 6,211,666 B1 | 4/2001 | Acker |
| 6,223,066 B1 | 4/2001 | Govari |
| 6,226,547 B1 | 5/2001 | Lockhart et al. |
| 6,230,038 B1 | 5/2001 | von Gutfeld et al. |
| 6,233,476 B1 | 5/2001 | Strommer et al. |
| 6,246,231 B1 | 6/2001 | Ashe |
| 6,341,231 B1 | 1/2002 | Ferre et al. |
| 6,366,799 B1 | 4/2002 | Acker et al. |
| 6,369,564 B1 | 4/2002 | Khalfin et al. |
| 6,370,417 B1 | 4/2002 | Horbaschek et al. |
| 6,374,131 B1 | 4/2002 | Tomita et al. |
| 6,374,134 B1 | 4/2002 | Bladen et al. |
| 6,377,041 B1 | 4/2002 | Jones, Jr. et al. |
| 6,400,139 B1 | 6/2002 | Khalfin et al. |
| 6,427,079 B1 | 7/2002 | Schneider et al. |
| 6,445,943 B1 | 9/2002 | Ferre et al. |
| 6,459,882 B1 | 10/2002 | Palermo et al. |
| 6,463,039 B1 | 10/2002 | Ricci et al. |
| 6,472,975 B1 | 10/2002 | Beigel et al. |
| 6,474,341 B1 | 11/2002 | Hunter et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,516,213 B1 | 2/2003 | Nevo |
| 6,528,991 B2 | 3/2003 | Ashe |
| 6,534,982 B1 | 3/2003 | Jakab |
| 6,553,326 B1 | 4/2003 | Kirsch et al. |
| 6,584,301 B1 | 6/2003 | Bohn et al. |
| 6,624,626 B2 | 9/2003 | Khalfin |
| 6,625,563 B2 | 9/2003 | Kirsch et al. |
| 6,636,757 B1 | 10/2003 | Jascob et al. |
| 6,656,135 B2 | 12/2003 | Zogbi et al. |
| 6,667,612 B2 | 12/2003 | Duret |
| 6,701,179 B1 | 3/2004 | Martinelli et al. |
| 6,711,429 B1 | 3/2004 | Gilboa et al. |
| 6,754,596 B2 | 6/2004 | Ashe |
| 6,762,600 B2 | 7/2004 | Khalfin |
| 6,774,624 B2 | 8/2004 | Anderson et al. |
| 6,782,285 B2 | 8/2004 | Birkenbach et al. |
| 6,783,536 B2 | 8/2004 | Vilsmeier et al. |
| 6,784,660 B2 | 8/2004 | Ashe |
| 6,803,757 B2 | 10/2004 | Slates |
| 6,812,842 B2 | 11/2004 | Dimmer |
| 6,833,814 B2 | 12/2004 | Gilboa et al. |
| 6,836,745 B2 | 12/2004 | Seiler et al. |
| 6,838,873 B2 | 1/2005 | James et al. |
| 6,856,823 B2 | 2/2005 | Ashe |
| 6,856,826 B2 | 2/2005 | Seeley et al. |
| 6,856,827 B2 | 2/2005 | Seeley et al. |
| 6,947,788 B2 | 9/2005 | Gilboa et al. |
| 6,968,846 B2 | 11/2005 | Viswanathan |
| 6,980,921 B2 | 12/2005 | Anderson et al. |
| 6,995,729 B2 | 2/2006 | Govari et al. |
| 7,015,859 B2 | 3/2006 | Anderson |
| 2001/0045826 A1 | 11/2001 | Schneider |
| 2001/0047133 A1 | 11/2001 | Gilboa et al. |
| 2002/0035321 A1 | 3/2002 | Bucholz et al. |
| 2002/0045812 A1 | 4/2002 | Ben-Haim et al. |
| 2002/0049375 A1 | 4/2002 | Strommer et al. |
| 2002/0193685 A1 | 12/2002 | Mate et al. |
| 2003/0120150 A1 | 6/2003 | Govari |
| 2003/0201767 A1 | 10/2003 | Khalfin |
| 2004/0011365 A1 | 1/2004 | Govari et al. |
| 2004/0019447 A1 | 1/2004 | Shachar |
| 2004/0068178 A1 | 4/2004 | Govari |
| 2004/0102696 A1 | 5/2004 | Govari |
| 2004/0129279 A1 | 7/2004 | Fabian et al. |
| 2004/0199072 A1* | 10/2004 | Sprouse et al. ............ 600/424 |
| 2004/0207389 A1 | 10/2004 | Nieminen et al. |
| 2004/0207528 A1 | 10/2004 | Fabian et al. |
| 2004/0210131 A1 | 10/2004 | Fukuda et al. |
| 2005/0003757 A1 | 1/2005 | Anderson |
| 2005/0004450 A1 | 1/2005 | Ben-Haim et al. |
| 2005/0012597 A1 | 1/2005 | Anderson |
| 2005/0015005 A1 | 1/2005 | Kockro |
| 2005/0049485 A1 | 3/2005 | Hammon et al. |
| 2005/0062469 A1 | 3/2005 | Anderson |
| 2005/0065433 A1 | 3/2005 | Anderson |
| 2005/0099290 A1 | 5/2005 | Govari |
| 2005/0107687 A1 | 5/2005 | Anderson |
| 2005/0165297 A1 | 7/2005 | Anderson et al. |
| 2005/0245821 A1 | 11/2005 | Govari et al. |
| 2005/0288574 A1 | 12/2005 | Thornton et al. |
| 2005/0288743 A1* | 12/2005 | Ahn et al. .................. 607/61 |
| 2006/0025668 A1 | 2/2006 | Peterson et al. |
| 2006/0030771 A1 | 2/2006 | Levine et al. |
| 2006/0055712 A1 | 3/2006 | Anderson |
| 2006/0058604 A1 | 3/2006 | Avinash et al. |

OTHER PUBLICATIONS

Christopher Nafis, Vern Jensen, Lee Beauregard, and Peter Anderson, "Method for estimating dynamic EM tracking accuracy of surgical navigation tools," Proceedings of SPIE, vol. 6141, pp. 152-167, Medical Imaging 2006: Visualization, Image-Guided Procedures, and Display, Mar. 2006.

F. H. Raab, E. B. Blood, T. O. Steiner, and H. R. Jones, "Magnetic Position and Orientation Tracking System," IEEE Transactions on Aerospace and Electronic Systems, vol. AES-15, No. 5, pp. 709-718, Sep. 1979.

Tom Ahlkvist Scharfeld, "An Analysis of the Fundamental Constraints on Low Cost Passive Radio-Frequency Identification System Design," Master's thesis, Massachusetts Institute of Technology, Cambridge, MA 02139, Aug. 2001.

* cited by examiner (Background)

CONFORMAL COIL ARRAY FOR A MEDICAL TRACKING SYSTEM

BACKGROUND

Medical practitioners, such as doctors, surgeons, and other medical professionals, often rely upon technology when performing a medical procedure, such as image-guided surgery or examination. A tracking or navigation system may provide positioning information of a medical instrument (such as a drill, a catheter, scalpel, scope, stent or other tools) with respect to the patient or a reference coordinate system. A medical practitioner may refer to the tracking system to ascertain the position of the medical instrument when the instrument is not within the practitioner's line of sight. A tracking system may also aid in pre-surgical planning.

The tracking (or navigation) system allows the medical practitioner to visualize the patient's anatomy and track the position and orientation (herein, "P&O") of the medical instrument. The medical practitioner may use the tracking system to determine when the instrument is positioned in a desired location. The medical practitioner may locate and operate on a desired or injured area while avoiding other anatomical structures.

Tracking systems may be ultrasound, inertial position, or electromagnetic tracking systems, for example. Known electromagnetic tracking systems employ coils as receivers and transmitters. The focus herein is on electromagnetic tracking systems (herein, "EM trackers"). In EM trackers, transmitter coil or coils emit quasi-static magnetic fields and receiver coil or coils measure the fields as received. From the field measurements and mathematical models of the coils, the P&O of the receiver with respect to the transmitter is determined. Alternatively, the P&O of the transmitter with respect to the receiver is determined. From this, the P&O of the medical instrument is determined with respect to the relevant anatomy of the patient.

EM trackers can be built with various coil architectures. Industry-standard-coil-architecture (ISCA) EM trackers use a trio of nearly-co-located nearly-orthogonal nearly-dipole coils for the transmitter and another trio of nearly-co-located nearly-orthogonal nearly-dipole coils for the receiver. Each coil trio is carefully characterized during manufacture to numerically express the precise value of the "nearly-" attribute in the previous sentence. From the field measurements and mathematical models of the coils, the P&O of the receiver with respect to the transmitter is determined. Alternatively, the P&O of the transmitter with respect to the receiver is determined. All six degrees of freedom (three of position and three of orientation) are tracked.

Single-coil EM trackers use a single dipole or nearly-dipole transmitter coil and an array of six or more receiver coils, or else use a single dipole or nearly-dipole receiver coil and an array of six or more transmitter coils. By electromagnetic reciprocity, these two arrangements function equivalently. The coils in the array may be dipole, nearly-dipole, or non-dipole coils (or combinations). The coils in the array are either precisely manufactured or precisely characterized during manufacture to obtain mathematical models of the coils in the array. The single coil does not need to be characterized.

From the field measurements and mathematical models, the P&O of the single coil with respect to the array are tracked. Since the single coil is symmetrical about its roll axis, only five degrees of freedom (three of position and two of orientation) of P&O are tracked. The gain of the single coil is also tracked.

The array of coils can be fabricated as a printed-circuit board or as an array of wound coils or as a combination of both. Arrangements of coils in the array vary widely in various implementations of single-coil EM trackers. The array may include electrically-conductive or ferromagnetic materials as part of the design of the array.

Typically, a tracker receiver unit (of course, this could be a transmitter unit) is attached to the to-be-tracked medical instrument. In addition, a tracker receiver unit is attached to other components that are also tracked. For example, with a conventional fluoroscopic image-guided procedure, one or more ISCA receivers are mounted on an X-ray image detector of the fluoroscope. When taking a fluoroscopic image, the tracking system tracks the X-ray image detector via the ISCA receivers mounted thereto. In this way, the tracker can determine the P&O of the X-ray image detector with respect to the relevant anatomy of the patient and, thus, be able to determine the relative P&O of other tracked medical instruments and components.

In addition to conventional fluoroscopic image-guided procedures, a tracker receiver unit is also attached to a surgical microscope for surgery, for example, inside the skull. In this exemplary application, an ISCA transmitter is rigidly fixed to the patient's skull to provide the dynamic reference to the patient's anatomy. One or more ISCA receivers are attached to the surgical instrument to track the P&O of the instrument with respect to the ISCA transmitter, and thus with respect to the patient's anatomy.

The real-time position and orientation of the instrument are superimposed on pre-operative images of the patient's anatomy. One or more ISCA receivers are mounted on the surgical microscope to permit tracking the microscope's line-of-sight with respect to the ISCA transmitter, and thus with respect to the patient's anatomy. The position of the microscope's focal point along the microscope's line-of-sight is read from the microscope. This information permits the position of the microscope's focal point to be determined with respect to the ISCA transmitter, and thus with respect to the patient's anatomy. The real-time P&O of the microscope's focal point and focal axis are then superimposed on pre-operative images of the patient's anatomy. The real-time P&O of the instrument are also superimposed on pre-operative images of the patient's anatomy.

In these exemplary contexts (conventional fluoroscopic image-guided procedures and microscope image-guided procedures) and other similar contexts, one major difficulty is the electrically-conductive materials and ferromagnetic materials (herein, "distorters") in the medical components distort the magnetic fields near the ISCA receivers mounted to those components. In the case of conventional fluoroscopic image-guided procedures, the distorters in the X-ray image detector distort the magnetic fields near the ISCA receivers mounted to the detector. In the case of conventional microscope image-guided procedures, the distorters in the microscope distort the magnetic fields near the ISCA receivers mounted to the microscope. ISCA EM trackers are very sensitive to such field distortion, leading to inaccurate tracking or, in extreme cases, a failure to track at all.

Two approaches are conventionally employed to ameliorate the distortion caused by the distorters in an image-capture component (such as an X-ray image detector or a surgical microscope): Distortion-mapping and calibration and spaced-mounting.

Distortion-mapping and calibration: The distortion caused by a detector's distorters is measured and mapped during a manufacturing-time-intensive robotic mapping procedure. In this way, the tracking errors are mapped and calibrated during use. Also, the limitations of accurate tracking can be determined before actual use. In other words, the accurate P&O of the detector might not be determinable under defined conditions.

Spaced-mounting. The ISCA receiver is rigidly mounted in a manner so as to put distance between the distorters of the detectors and the receiver itself. In this way, the receiver is spaced away from the surface of the detector to reduce the effects of field distortion. This conventional approach is illustrated in FIG. 1. An image-capture component 100 is generically shown as a box. Examples of an image-capture component include an x-ray image detector or a surgical microscope. A mounting-bracket 110 attaches an EM receiver 120 to the image-capture component 100. The mounting-bracket 110 is designed so that the EM receiver 120 is physically spaced away from the surface of the image-capture component 100 (and its distorters therein).

Consequently, in the conventional approach, the following occurs in an effort to reduce the effects of distortion caused by the distorters in image-capture components:

The image-capture component cannot be tracked in some desired positions and orientations.
The receivers stick out from the image-capture component, so get in the way.
An expensive mapping manufacturing process is necessary.

SUMMARY

Described herein are one or more implementations for reducing the effects of distortion caused by the distorters in medical image-capture components used in medical electromagnetic tracking system. Examples of a medical image-capture component include an X-ray image detector used in fluoroscopic image-guided medical procedures and a surgical microscope. With one or more implementations described herein, the electromagnetic receiver unit (or transmitter unit) is conformally attached to the medical image-capture component.

This summary itself is not intended to limit the scope of this patent and the appending claims of this patent. Moreover, the title of this patent is not intended to limit the scope of this patent. For a better understanding of the present invention, please see the following detailed description and appending claims, taken in conjunction with the accompanying drawings. The scope of the present invention is pointed out in the appending claims.

BRIEF DESCRIPTION OF THE DRAWINGS

The same numbers are used throughout the drawings to reference like elements and features.

DETAILED DESCRIPTION

One or more implementations, described herein, are for reducing the effects of distortion caused by the distorters in medical image-capture components used in medical electromagnetic tracking system. Examples of a medical image-capture component include an X-ray image detector used in fluoroscopic image-guided medical procedures and a surgical microscope. With one or more implementations described herein, the electromagnetic receiver unit (or transmitter unit) is conformally attached to the medical image-capture component.

Using one or more implementations described herein, medical image-capture components can be tracked in a broader range of space than conventional approaches allow. Furthermore, the needs for expensive and time-consuming distortion-mapping for each instance is reduced or eliminated.

Exemplary Electromagnetic Tracking System

Figure 2:
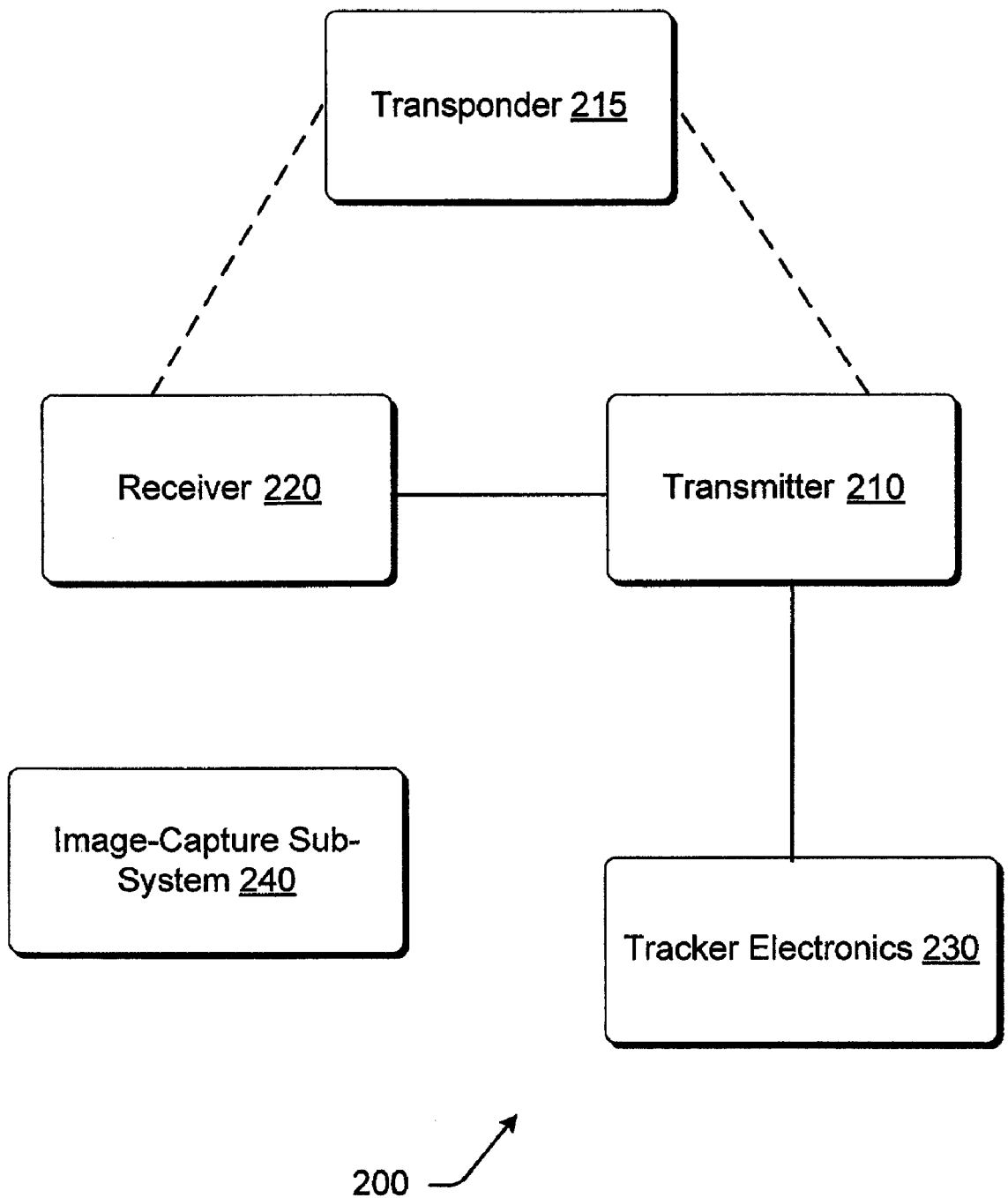
FIG. 2 shows an electromagnetic tracking system in accordance with one or more implementations described herein.

FIG. 2 illustrates an exemplary electromagnetic tracking system ("tracker") 200 used in accordance with an embodiment described herein. The tracker 200 includes a transmitter 210, a transponder 215, a receiver 220, and tracker electronics 230. The transmitter 210 emits a transmitter signal. The transponder 215 receives the transmitter signal and emits a transponder signal. The receiver 220 detects the transmitter signal and the transponder signal. The tracker electronics 230 analyzes the signals received by the receiver 220 to identify the transponder 215 and determine a position of the transponder 215. FIG. 2 also shows an image-capture sub-system 240 which may be used in coordination with the tracking system.

In at least one described embodiment, the transponder 215 is a single-coil transponder. The transponder 215 may be a battery-powered wireless transponder, a passive transponder, or a single-coil wired transponder.

During some medical procedures, portions of medical instruments may be obscured or covered by portions of a patient's anatomy. For example, a small incision may be made in a patient's abdomen and a medical instrument such as a needle and trocar inserted in the incision. After the needle and trocar is inserted through the incision, the surgeon can not see the portion of the needle and trocar that is within the patient's abdomen.

In order to guide the tip of the needle to a desired region of interest, a transponder may be placed near the tip of the needle. A transmitter can emit a transmitter signal that propagates through the patient's anatomy. The transmitter signal impinges upon the transponder located on the tip of the needle. In response, the transponder emits a transponder signal.

A receiver receives the transponder signal. A tracking system coupled to the receiver processes the transponder signal. The tracking system can use the transponder signal to calculate the location of the transponder. Consequently, the transmitter, transponder, receiver, and tracking system can be used to identify and locate portions of medical instruments during a medical procedure and to aid in navigating the medical instruments to regions of interest.

Exemplary Conformal Electromagnetic Tracker

Figure 1:
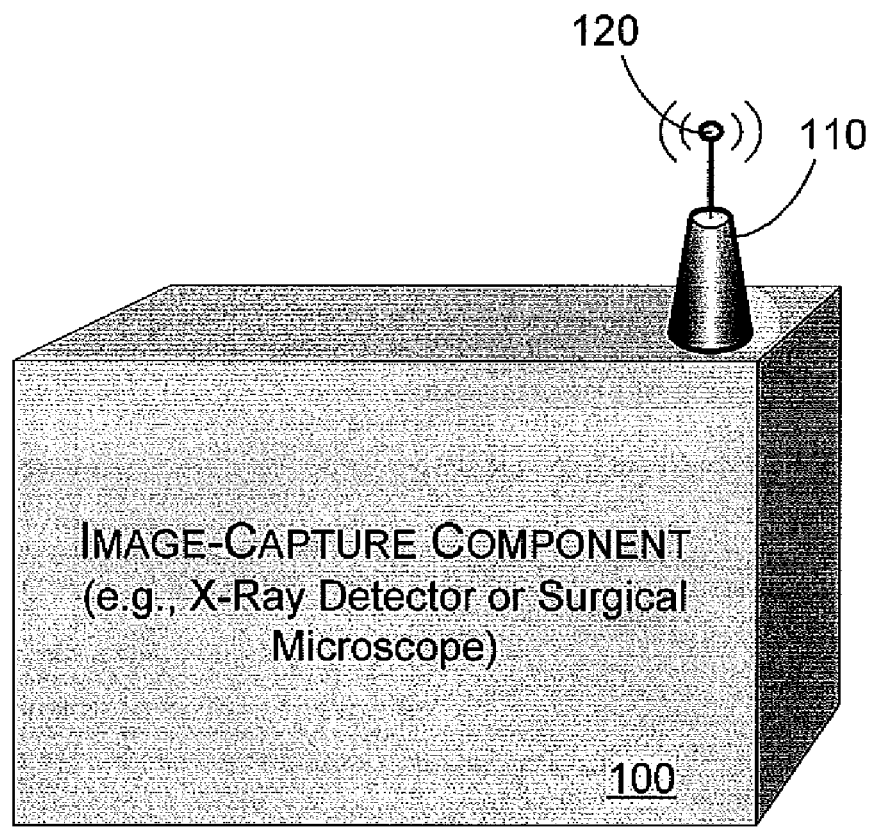
FIG. 1 shows a graphic representation of a conventional arrangement of an electromagnetic tracker receiver unit and an image-capture component.
Figure 3:
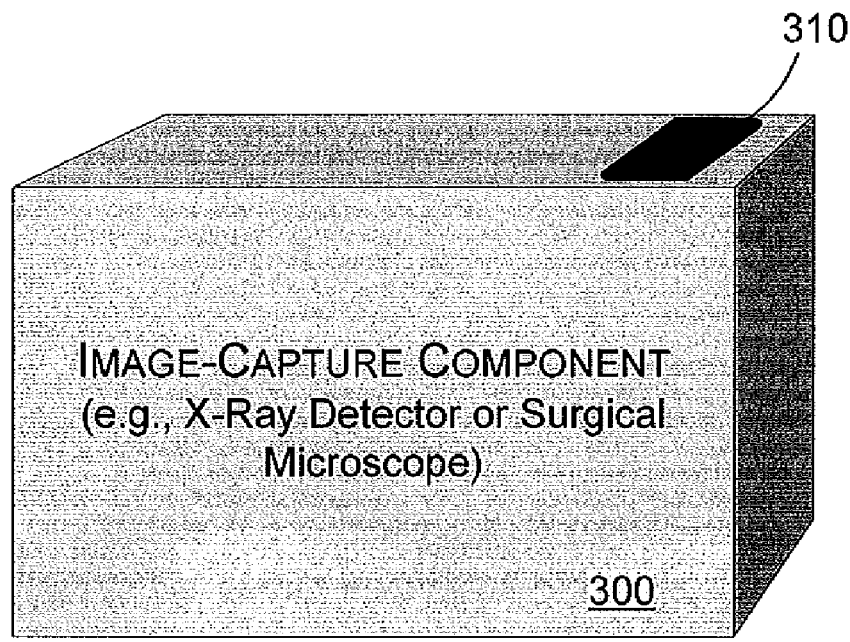
FIG. 3 shows a graphic representation of a new arrangement, in accordance with one or more implementations described herein, of an electromagnetic tracker receiver unit and an image-capture component.

FIG. 3 shows, for the purpose of illustration, an exemplary image-capture component 300 and shows the component generically as a box. Examples of an image-capture component include an X-ray image detector or a surgical microscope. Rather than having a mounting-bracket (like bracket 110 shown in FIG. 1), an EM receiver 310 is mounted directly to the image-capture component 300. More precisely, the EM receiver 310 is attached to the image-capture component 300 so that is conforms the surface of the component over the area that is attached. This may be conformally attached or mounted. Conformal mounting eliminates the field-distorting effects of the distorters of the conventional image-capture component 100. The EM receiver 310 shown in FIG. 3 may be the receiver 220 shown in FIG. 2.

A disadvantage of single-coil EM trackers is the need to find a place to put the array of coils. To work best, this array needs to be physically spread out in space. Note that a multi-channel single-coil EM tracker can track two or three single coils simultaneously. If two or more single coils are mounted rigidly with respect to each other with their axes pointed in different directions, and tracked as two or more single coils or as a group, all six degrees of freedom can be tracked for the set of single coils.

With one or more implementations described herein, the EM receiver 310 may be a coil array. Also, a multi-channel single-coil EM tracker may be used to track the coil array. This coil array is built to conform to the surface of the image-capture component 300 in a manner that incorporates the field-distorting effects and mechanical requirements into the array design. In this way, measurements taken at just a few points are sufficient to accurately characterize the fields produced by a particular instance (i.e., particular serial number) of a given type of array.

X-ray detectors and microscopes having housings built of electrically-conductive material to prevent electromagnetic interference to the innards of the detector or microscope. Electrically-conductive metals have excellent mechanical properties for building rigid structures. Thus, coil arrays placed on electrically-conductive sheets are appropriate for placement on the housings.

If a solenoidal coil is laid against an electrically-conductive sheet with the axis of the coil parallel to the sheet, the magnetic image of the coil is parallel to and next to the coil. Thus the magnetic field emitted by the coil is increased over the field without the sheet. This is well-known in electromagnetics.

If a solenoidal coil is wound around a long thin ferromagnetic rod, the resulting coil is large-dimension along the coil axis (the length of the rod), and is small-dimension along the other two axes. For example, a coil of 15000 turns of #56 wire is wound on a ferromagnetic core 0.5 millimeters in diameter and 8 millimeters long, resulting in a solenoidal coil 2 millimeters in diameter and 8 millimeters long.

Thus, one or more such coils placed against the surface of the housing of the image-capture component 300, will occupy little height away from the housing.

Conformal attachment also includes the concept of "flush mounting." A notch or alcove may be formed out of the housing of the image-capture component 300. That alcove is shaped to receive the EM receiver 310 therein so that the exposed surface of the receiver now conforms to the remaining surface of the component. This is flush mounting. A flush mounted EM receiver 310 will still have satisfactory field emission.

Other Applications, Implementations, and Details

The discussion herein focuses on the specifics of a medical tracking or navigational system, especially on used to track medical instruments in a patient's anatomy. However, the details of these described specifics are merely exemplary.

The functionality of the described implementations may and can be employed in variety of applications where it is desirable to accurately track the position of items other than medical instruments in a variety of applications. That is, a tracking system may be used in other settings where the position of an instrument in an object or an environment is difficult to accurately determine by visual inspection.

For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems may be used to monitor the position of a person in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Recall that, by reciprocity, the mutual inductance of two coils is the same, whichever coil is the transmitter and which is the receiver. Therefore, unless the context indicates otherwise, the reader should understand that when transmitters and receivers are discussed herein, the relative positioning and functionality of the receivers and transmitters may be swapped. Because of mutual inductance the functionality of the implementation with swapped receivers and transmitters remains the same as an implementation where there is no swapping of the receivers and transmitters.

Furthermore, the techniques, described herein, may be implemented in many ways, including (but not limited to) medical devices, medical systems, program modules, general- and special-purpose computing systems, network servers and equipment, dedicated electronics and hardware, and as part of one or more computer networks.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

The invention claimed is:

1. A medical tracking system comprising:
   an image-capture sub-system configured to capture images during a medical procedure;
   an electromagnetic tracking sub-system configured to track one or more medical instruments and one or more image-capture components of the image-capture sub-system during a medical procedure;
   a tracker unit conformally mounted to one of the image-capture components of the image-capture sub-system that is being tracked by the electromagnetic tracking sub-system, wherein the tracker unit is conformally mounted so that the unit conforms to a surface of the image-capture component to which the unit is mounted.

2. A system as recited in claim 1, wherein the tracker unit is a receiver.

3. A system as recited in claim 1, wherein the tracker unit is a transmitter.

4. A system as recited in claim 1, wherein the image-capture component to which the unit is mounted has a housing comprising electrically-conductive material.

5. A system as recited in claim 1, wherein the conformally mounted tracker unit is flush mounted to the one of the image-capture components.

6. A system as recited in claim 1, wherein image-capture sub-system is an X-ray image detector.

7. A system as recited in claim 1, wherein image-capture sub-system is a surgical microscope.

8. A tracker apparatus comprising a receiver mounted to an image-capture component of an image-capture sub-system, the image-capture component being tracked by an electromagnetic tracking sub-system, the image-capture sub-system configured to capture images during a medical procedure, the electromagnetic tracking sub-system configured to track one or more medical instruments and one or more image-capture components of the image-capture sub-system during a medical procedure, wherein the receiver is conformally mounted so that the receiver conforms to a surface of the image-capture component.

9. An apparatus as recited in claim 8, wherein the image-capture component to which the receiver is mounted has a housing comprising electrically-conductive material.

10. An apparatus as recited in claim 8, wherein image-capture sub-system is an X-ray image detector.

11. An apparatus as recited in claim 8, wherein image-capture sub-system is a surgical microscope.

12. A tracker apparatus comprising a transmitter mounted to an image-capture component of an image-capture sub-system, the image-capture component being tracked by an electromagnetic tracking sub-system, the image-capture sub-system configured to capture images during a medical procedure, the electromagnetic tracking sub-system configured to track one or more medical instruments and one or more image-capture components of the image-capture sub-system during a medical procedure, wherein the transmitter is conformally mounted so that the transmitter conforms to a surface of the image-capture component.

13. An apparatus as recited in claim 12, wherein the image-capture component to which the transmitter is mounted has a housing comprising electrically-conductive material.

14. An apparatus as recited in claim 12, wherein image-capture sub-system is an X-ray image detector.

15. An apparatus as recited in claim 12, wherein image-capture sub-system is a surgical microscope.

* * * * *